US012295755B2

(12) United States Patent
van der Hoeven (10) Patent No.: US 12,295,755 B2
(45) Date of Patent: May 13, 2025

(54) FACE SHIELD AND TRACKING SYSTEM (71) Applicant: Martin van der Hoeven, Irvine, CA (US)

(72) Inventor: Martin van der Hoeven, Irvine, CA (US)

( * ) Notice: Subject to any disclaimer, the term of this patent is extended or adjusted under 35 U.S.C. 154(b) by 945 days.

(21) Appl. No.: 17/350,257

(22) Filed: Jun. 17, 2021

(65) Prior Publication Data
US 2021/0392974 A1 Dec. 23, 2021

Related U.S. Application Data (60) Provisional application No. 63/040,444, filed on Jun. 17, 2020.

(51) Int. Cl.
 *A61B 5/00* (2006.01)
 *A41D 13/11* (2006.01)
 *A61B 5/01* (2006.01)
 *A62B 23/02* (2006.01)
 *G06F 1/16* (2006.01)
 *G06F 3/01* (2006.01)

(52) U.S. Cl.
 CPC .......... *A61B 5/746* (2013.01); *A41D 13/1107* (2013.01); *A41D 13/1146* (2013.01); *A41D 13/1161* (2013.01); *A41D 13/1184* (2013.01); *A61B 5/01* (2013.01); *A61B 5/6803* (2013.01); *A62B 23/02* (2013.01); *G06F 1/163* (2013.01); *G06F 3/011* (2013.01)

(58) Field of Classification Search
 CPC ....... A62B 18/02; A62B 18/08; A62B 18/082; A62B 18/084; A62B 18/086; A62B 23/02; A41D 13/1184
 See application file for complete search history.

(56) References Cited

U.S. PATENT DOCUMENTS

| | | | | | |
|---|---|---|---|---|---|
| 3,015,105 | A | * | 1/1962 | Rogowski | A45D 44/12 2/9 |
| 3,152,588 | A | * | 10/1964 | Rogowski | A62B 18/02 2/9 |
| 3,678,929 | A | * | 7/1972 | Buscher | A41D 13/1184 2/427 |
| 4,207,882 | A | * | 6/1980 | Lemere | A62B 18/00 2/9 |
| 6,199,550 | B1 | * | 3/2001 | Wiesmann | G08B 21/0453 128/204.23 |

(Continued)

FOREIGN PATENT DOCUMENTS

| | | | | | |
|---|---|---|---|---|---|
| CN | | 111035870 A | * | 4/2020 | |
| FR | | 3109698 A1 | * | 11/2021 | ......... A41D 13/1138 |

(Continued)

*Primary Examiner* — Kathryn E Ditmer
(74) *Attorney, Agent, or Firm* — Chang & Hale LLP (57) ABSTRACT

A face shield includes a molded body portion configured to cover a wearer's eyes, nose, mouth, and chin. The body portion, which is secured to the wearer's ears by a pair of connector elements, includes at least one opening containing a replaceable filter. The face shield may part of a tracking system including multiple face shields, wherein each face shield includes a sensor that transmits data to a processor that in turn analyzes and interprets the data and transmits the results to a display device.

9 Claims, 10 Drawing Sheets

(56) References Cited

U.S. PATENT DOCUMENTS

| | | | | |
|---|---|---|---|---|
| 6,374,424 B1* | 4/2002 | Tredup | ............... | A41D 13/1184 |
| | | | | 2/427 |
| 7,640,933 B1* | 1/2010 | Ho | ................... | A61M 16/0622 |
| | | | | 128/206.28 |
| 7,958,889 B1* | 6/2011 | Fernandez-DeCastro | ................... | |
| | | | | A41D 13/11 |
| | | | | 128/205.27 |
| 9,895,592 B2* | 2/2018 | Emard | ................... | A63B 71/10 |
| 9,999,739 B2* | 6/2018 | Hendriks | .......... | A61M 16/0605 |
| 10,973,267 B1* | 4/2021 | Correa | ..................... | A61B 5/01 |
| 10,980,296 B1* | 4/2021 | Hosac | ................... | A62B 18/10 |
| 2004/0003810 A1* | 1/2004 | Templeton | ............. | A62B 17/04 |
| | | | | 128/201.25 |
| 2004/0163648 A1* | 8/2004 | Burton | ................ | A61M 16/0605 |
| | | | | 128/204.21 |
| 2006/0201511 A1* | 9/2006 | Freriks | ................... | A62B 17/04 |
| | | | | 128/206.13 |
| 2009/0151734 A1* | 6/2009 | Park | ....................... | A61K 33/32 |
| | | | | 128/206.17 |
| 2010/0126504 A1* | 5/2010 | Johnstone | ............... | A61F 9/029 |
| | | | | 128/202.13 |
| 2014/0005497 A1* | 1/2014 | Larsen | ................ | A61B 5/0816 |
| | | | | 600/549 |
| 2016/0332008 A1* | 11/2016 | McAndrews | ........ | A62B 18/025 |
| 2017/0100612 A1* | 4/2017 | Conge | ..................... | A62B 17/04 |
| 2018/0036563 A1* | 2/2018 | Bora | ....................... | A61F 9/029 |
| 2018/0190029 A1* | 7/2018 | Stein | ...................... | G06F 3/011 |
| 2018/0296864 A1* | 10/2018 | Feasey | ................ | A62B 18/003 |
| 2018/0311515 A1* | 11/2018 | Wilson | ................ | A61B 5/6803 |
| 2020/0121005 A1* | 4/2020 | Belousov | ........... | A41D 13/1107 |
| 2021/0219636 A1* | 7/2021 | Stroiazzo-Mougin | ...................... | |
| | | | | A62B 23/02 |
| 2021/0345706 A1* | 11/2021 | Kaltenbach | ........ | A41D 13/1161 |
| 2021/0381023 A1* | 12/2021 | Tran | ................... | G01N 33/5302 |
| 2021/0393140 A1* | 12/2021 | Rein | ................. | A41D 13/1184 |

FOREIGN PATENT DOCUMENTS

| | | | | | |
|---|---|---|---|---|---|
| FR | | 3110819 A1 | * | 12/2021 | |
| KR | | 20160089185 | * | 7/2016 | |
| KR | | 20190057917 A | * | 5/2019 | |
| WO | WO-2011121525 A1 | | * | 10/2011 | ............ A61M 16/06 |
| WO | WO-2012033394 A1 | | * | 3/2012 | ......... A41D 13/1184 |
| WO | WO-2017146382 A1 | | * | 8/2017 | ............ A62B 18/04 |
| WO | WO-2018220516 A1 | | * | 12/2018 | |

* cited by examiner

FACE SHIELD AND TRACKING SYSTEM

CROSS-REFERENCE TO RELATED APPLICATIONS

This application claims priority from U.S. Provisional Application No. 63/040,444, filed Jun. 17, 2020. The contents of that provisional application are hereby incorporated herein by reference.

TECHNICAL FIELD

The present disclosure relates in general to personal protective equipment and more particularly to a face shield having integrated filters and smart wearable technology, and to a tracking system for monitoring individuals wearing the face shield.

BACKGROUND

Facial protection for medical workers and laypeople in a potentially virus-contaminated environment falls into three major categories: face masks, face shields, and goggles.

Surgical masks and N95 respirators are two well-known types of medical face masks. Surgical masks, which have been in existence for over 100 years, are made from disposable fluid-resistant material and can protect the wearer from large forward droplets, splashes, or sprays of hazardous fluid. They may also protect others from the wearer's respiratory emissions. However, because these masks are somewhat loose-fitting and do not form a tight seal with the wearer's face, they do not offer adequate protection from incoming small aerosols or even from larger aerosols that may enter from the sides. N95 respirators are tighter and are made from a disposable material that filters out smaller airborne particles. When properly fitted, they are more effective than surgical masks at protecting the wearer from incoming virus particles, but they can impede the wearer's breathing and thus may be unsuitable for people with chronic respiratory, cardiac or other medical conditions. In addition, the N95 was designed for short time use by professional medical and hazardous workers, requiring extreme tight fitting for a few hours, not all day use. Moreover in times of pandemic, surgical masks and N95 respirators may be in short supply and limited to use only by medical professionals. Laypeople then must rely on fabric masks, which are considerably less effective than either surgical masks or N95 respirators at filtering out virus-laden aerosols. Still another shortcoming of face masks is that virus droplets accumulate in the filters which increases the chances of contamination when a filter is touched. In addition, none of the above-described face masks provide eye protection, so the wearer needs to wear goggles in addition to a mask.

Conventional face shields are non-porous, making them effective at stopping droplets and aerosols coming from directly in front of or behind the shield, but they cannot stop contaminated air from traveling around the shield and entering or exiting the wearer's facial area from above, below, or the sides. As a result, conventional face shields are not usually used alone, but are worn in conjunction with a mask and goggles.

Multiple barriers are needed for resisting the flow of contaminated air. However, current surgical masks, N-95 respirators, and face shields are designed to provide only a single barrier. Furthermore, none of these current PPE devices include sensors for tracking motion data or recording metrics about individual wearers or groups of wearers; nor do they offer user-to-user communication.

The above and other shortcomings of existing face masks and shields are addressed by the present disclosure as summarized below.

SUMMARY

A face shield according to the present invention includes a molded body portion configured to cover a wearer's eyes, nose, mouth, and chin. The body portion, which is secured to the wearer's ears by a pair of connector elements, includes at least one opening containing a replaceable filter. The face shield may also be provided with a seal that surrounds the opening and is configured to sealingly engage the wearer's nose, cheeks, and chin. The back edge of the mask may include baffles configured to direct air flow through circuitous paths and to stop or slow the movement of any aerosols that have passed through or around the filters and seals.

In some embodiments, the molded body portion may include substantially planar eye regions configured to align with the wearer's eyes, a sloped nose region projecting outwardly relative to the eye regions and configured to align with the wearer's nose, and cheek regions on either side of the nose region, each cheek region including a filtered opening. A fairing containing a virus containment chamber may communicate with the filtered opening of each cheek region. The rear end of the virus containment chamber may communicate with a filtered port in the rear portion of the fairing. Each fairing may include a side wall defining an entry scoop configured to direct incoming and outgoing air into the virus containment chamber.

In some embodiments, the connector elements may be adjustably secured to the body portion of the face shield.

In some embodiments, the body portion may be formed of a transparent plastic material.

In some embodiments, an inertial motion capture unit may be embedded into the face shield.

In some embodiments, a temperature sensor may be embedded into the face shield.

In some embodiments, the face shield may include a hinged door that provides access to the wearer's mouth, allowing the wearer to eat and drink without removing the shield.

The face shield may part of a tracking system including multiple face shields, wherein each face shield includes a sensor configured to transmit data to a processor programmed to analyze and interpret the data. Output from the processor is transmitted to a display device having a graphical user interface programmed to display metrics pertaining to the shields, their users, and their environments. The data may include location and orientation data captured by an inertial motion capture unit in the face shield, and/or temperature data captured by a temperature sensor in the face shield. The data from an inertial motion capture unit may be used to determine whether and how long specific users are wearing their masks, while the temperature data may be used to determine if a user is ill. If the system detects that a user is not wearing their mask, is ill, or that any other type of potentially risky situation has arisen, a warning message or alert may be displayed on the display device.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
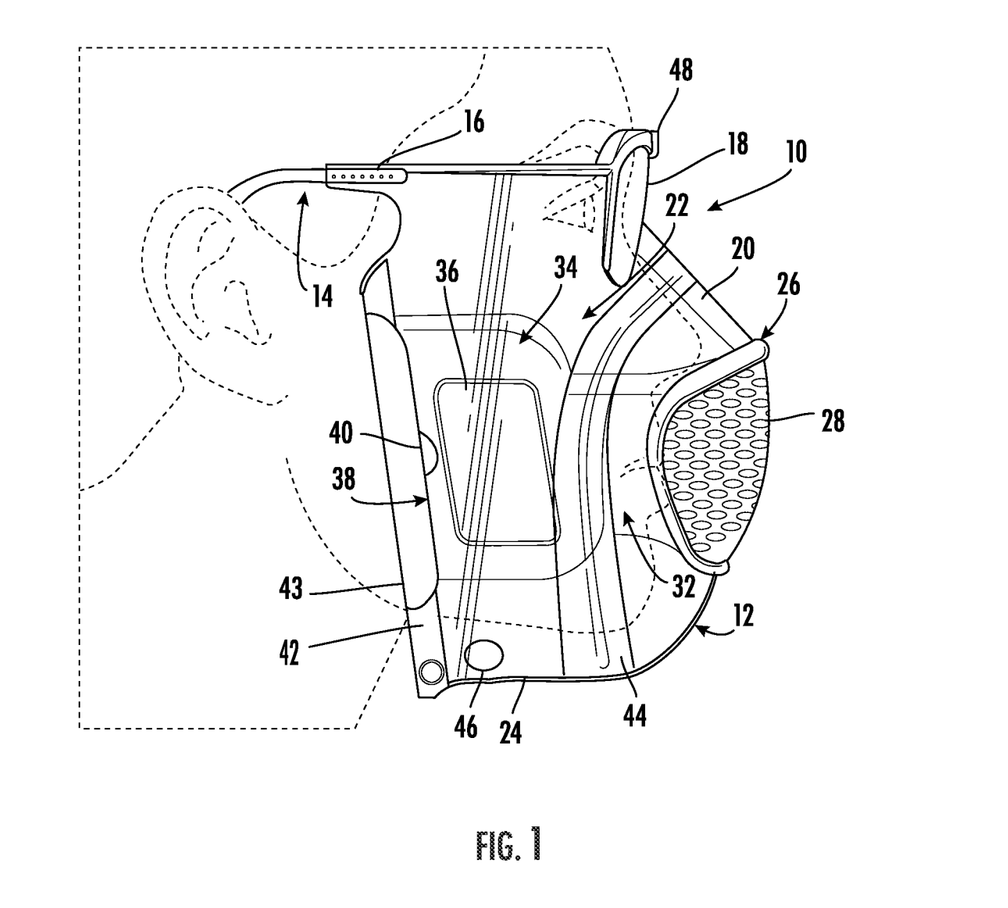
FIG. 1 is an outer side view showing a face shield.

FIG. 1 is a side view of an individual wearing one example of a face shield 10 according to the present disclosure. The face shield 10 is symmetrical about the wearer's face; thus, any element shown on this side of the viewer's face is repeated on the opposite side. The face shield 10 includes a molded body portion 12 that covers the wearer's eyes nose, mouth and chin, and is secured to the wearer's ears by connectors 14. In this embodiment, the ear connectors are in the form of a pair of relatively rigid temples, each of which includes an outwardly projecting adjustment pin that may be received in any one of a plurality of mating holes 16 formed along the upper edge of the body portion 12, thereby allowing the wearer to adjust the distance between the face shield 10 and her face. In other embodiments, the connectors may be flexible ear loops.

The body portion 12, which is preferably transparent and made from a strong, flexible, and easily cleanable plastic such as polycarbonate or polyethylene, is contoured to resemble a human face. It includes substantially planar eye regions 18 configured to align with the wearer's eyes, a sloped nose region 20 configured to align with the wearer's nose, cheek regions 22 on either side of the nose region 20, and a chin region 24 that completely or nearly completely surrounds the wearer's chin. In this example, openings 26, each containing a filter 28, are provided below and on either side of the nose region 20 and are configured to be laterally aligned with the wearer's mouth. However, the number of openings may vary; in another example, the body portion 12 may include a single opening located directly in front of the wearer's mouth.

Each filtered opening 26 communicates with an air flow channel 32 which in turn communicates with a virus containment compartment housed in a fairing 34 formed to the rear of the opening 26. The outer surface of the fairing 34 may include a recessed area 36 for receiving a label that personalizes the face shield. A port 38 formed in the rear of the fairing 36 also communicates with the virus containment channel and contains a filter 40. A series of baffles 42 runs along the entire back edge 43 of the face shield 10.

The inner surface of the body portion 10 includes a recess for receiving a padded, moisture-absorbent seal 44 configured to surround the wearer's nose, mouth, and chin. The seal 44 is removable, allowing it to be replaced or cleaned and reused.

A Bluetooth-enabled inertial motion capture unit (IMU) 46 may be embedded into one side of the face shield 10. The IMU measures and records data such as the location, acceleration, orientation, and angular rate, and may transmit the information to a processor in a face shield tracking system. The processor may be programmed to interpret the data recorded by the IMU to determine whether and how long the shield is being worn. Output from the processor may then transmitted to a display device, such as a mobile phone, laptop computer, tablet, or augmented reality (AR) glasses, having a graphical user interface programmed to receive output from the processor and to display messages about the status of the mask to a user.

A temperature sensor 48 may also be embedded into the face shield 10 at a location above and between the eye regions 18. The temperature sensor may measure the wearer's body temperature and may transmit it to the processor in the face shield tracking system, which then transmits an alert to the display device, notifying the user if the wearer has an elevated temperature.

Sensors for detecting specific types of viruses, bacteria, or other pathogens could also be incorporated into the face shield.

Figure 2:
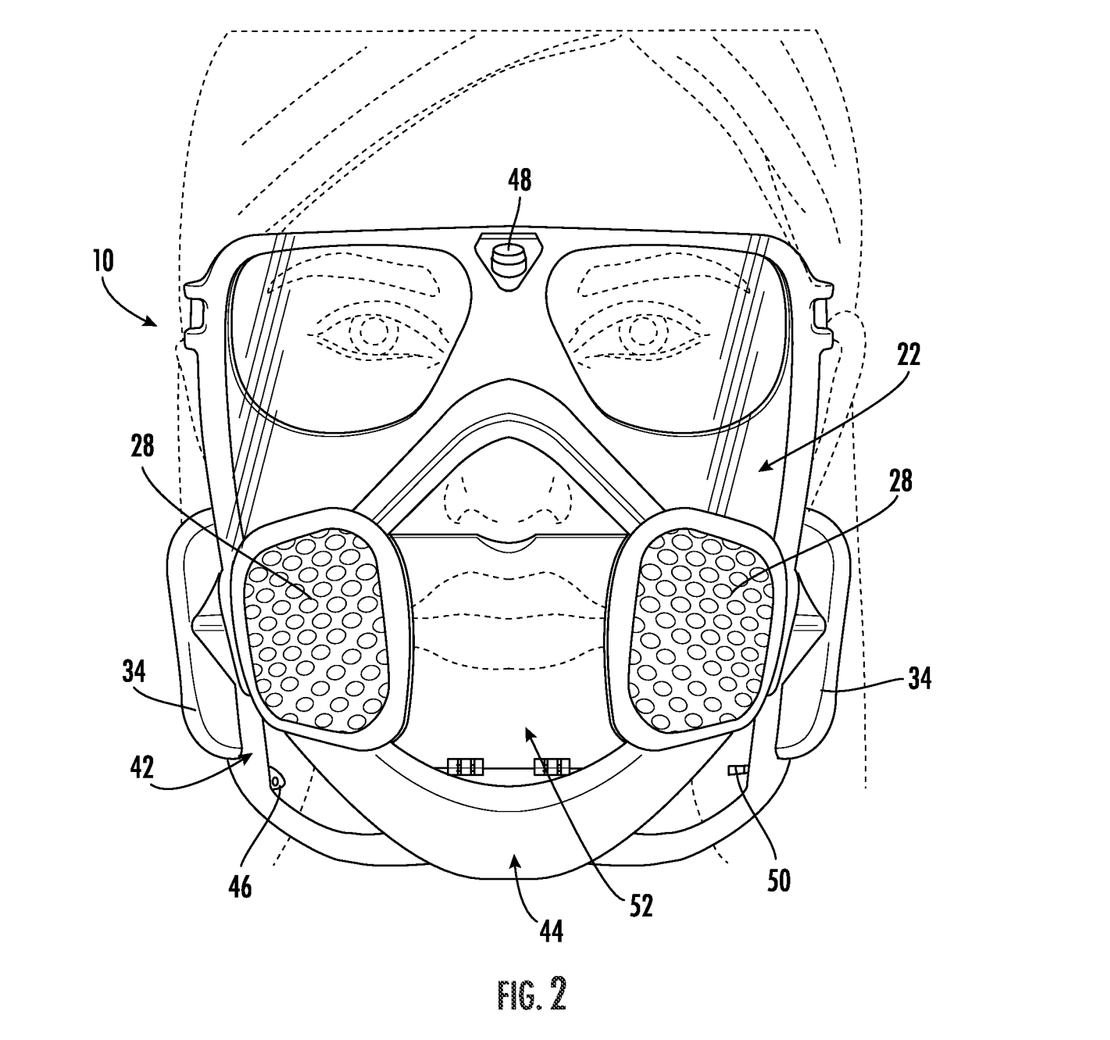
FIG. 2 is a front view of FIG. 1.

FIG. 2 is a front view of the face shield 10, showing the front filters 28, the fairings 34 containing virus containment compartments, baffles 42, seal 44, IMU 46, and temperature sensor 48, as described above. A bar code 50 or other electronically readable identifier is provided on the side of the mask opposite the IMU. The bar code 50 identifies the mask owner and can be scanned when the wearer enters their workplace, school, or other monitored location.

The face shield 10 also includes a hinged door 52 bounded on its sides by the front filters 28 and on its upper edge by the wearer's nose. The door 52, which opens downwardly, allows the wearer to eat and drink without having to remove the face shield 10.

Figure 3:
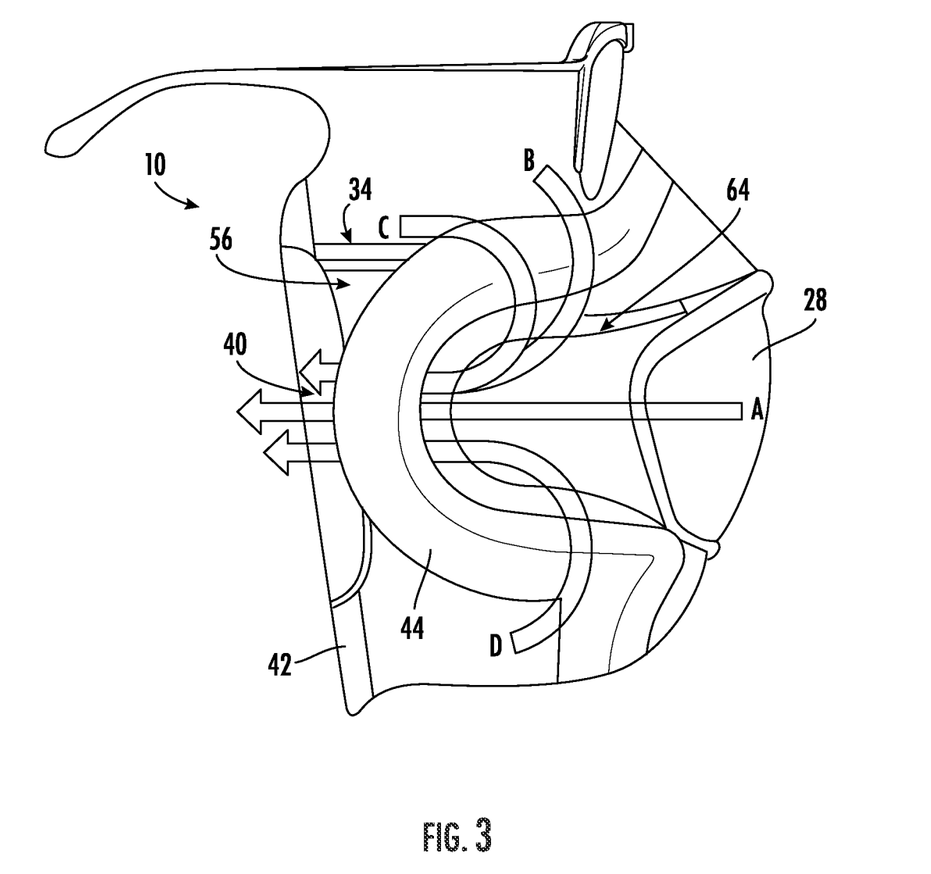
FIG. 3 is an inner side view of the face shield shown in FIGS. 1 and 2.

FIG. 3 is an inner view, with arrows A, B, C, and D showing the flow of air through the face shield 10. The inner side wall of each fairing 34 defines an entry scoop 54 that directs air entering through front filter 28 or traveling around seal 44 into the virus containment chamber 56 and through the associated rear filter 40.

Figure 4:
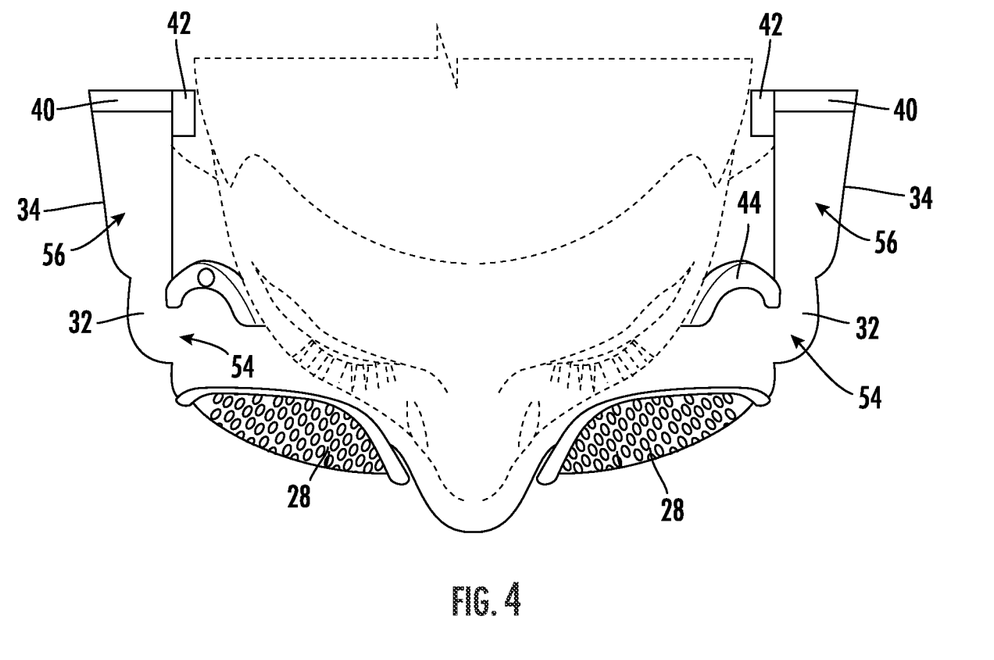
FIG. 4 is a top view of the face shield.

FIG. 4 is a top view showing the front filters 28, air flow channels 32, rear filters 40, baffles 42, seal 44, and entry scoops 54 leading to virus containment chambers 56. From here it can be seen that nearly all air exhaled from the mask wearer's mouth or nose will either exit directly through the front filters 28 or will pass through the entry scoops 54, air flow passages 32, and virus containment chambers 56 before finally exiting through the rear filters 40. Any air that instead leaks through the seal 44 will pass through baffles 42.

Figure 5:
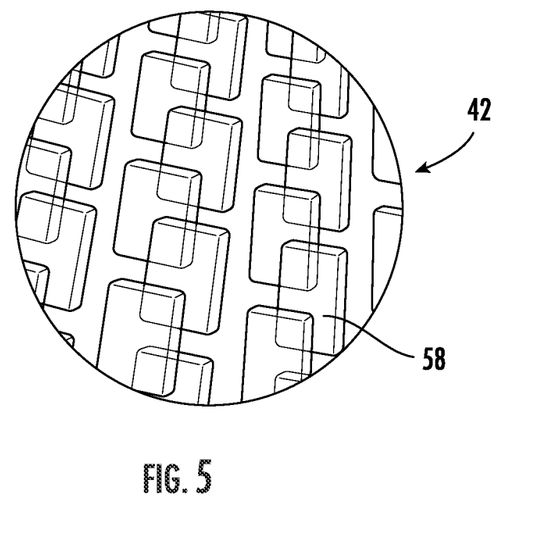
FIG. 5 is a detail of a baffled edge of the face shield, viewed from the front.
Figure 6:
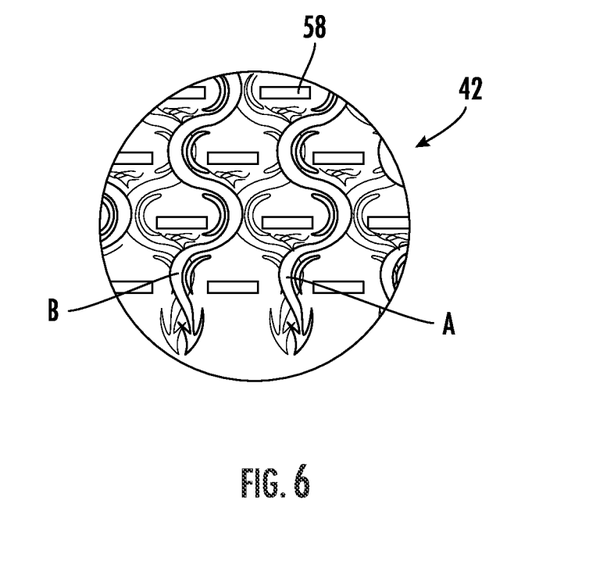
FIG. 6 is a detail of a baffled edge of the face shield, viewed from the top.

FIG. 5 is an enlarged front detail view showing baffles 42 of the face shield. The baffles 42 include a plurality of (at least four) rows and columns of plates 58 that are offset from one another to create circuitous flow paths, as shown by arrows A, B in the top view of FIG. 6. As the air flows through these circuitous paths, any virus-containing aerosols carried by the currents of air are likely to strike the surfaces of the plates 58 and to remain on these surfaces rather than escaping into the environment.

Figure 7:
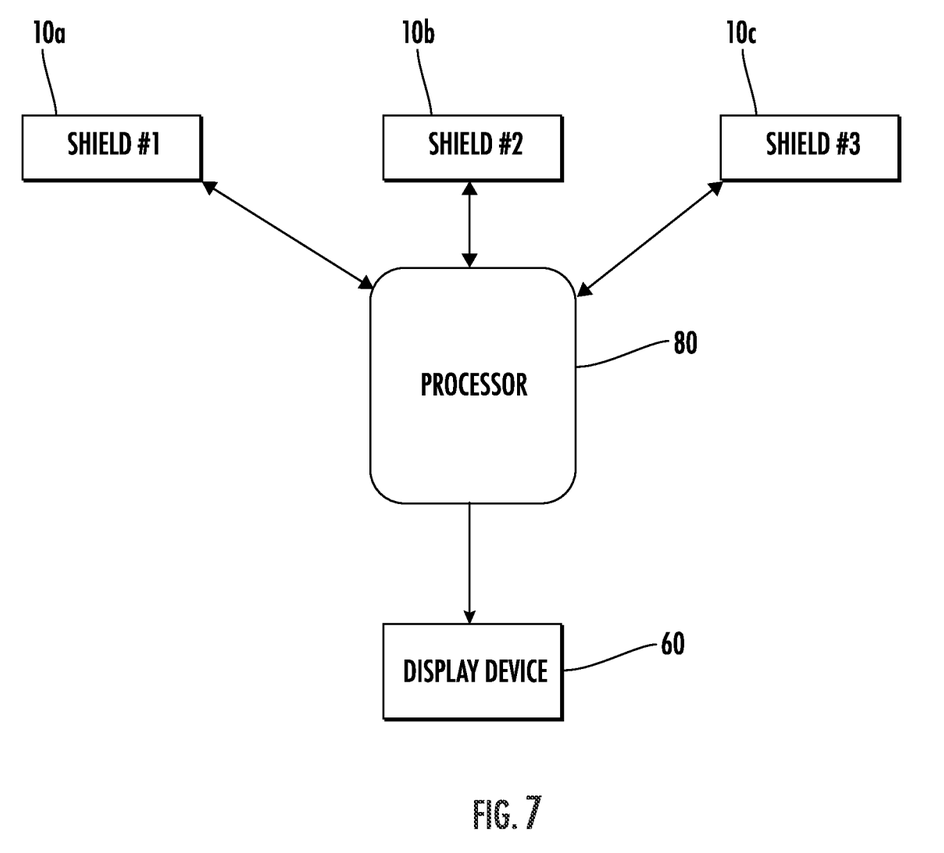
FIG. 7 is a sample block diagram of a face shield tracking system.

FIG. 7 shows a tracking system which may incorporate a face shield of the type described above. The system includes face shields 10a,b,c, a processor 80, and a display device 60 such as a cell phone, laptop computer, or tablet having a graphical user display. The tracking system may be used by large institutions such as hospitals and schools that wish to monitor whether their staff and others are complying with regulations regarding personal protective equipment. Metrics may be collected and displayed for individual wearers or for the population as a whole. The system may allow user-to-user communication as well.

Figure 8:
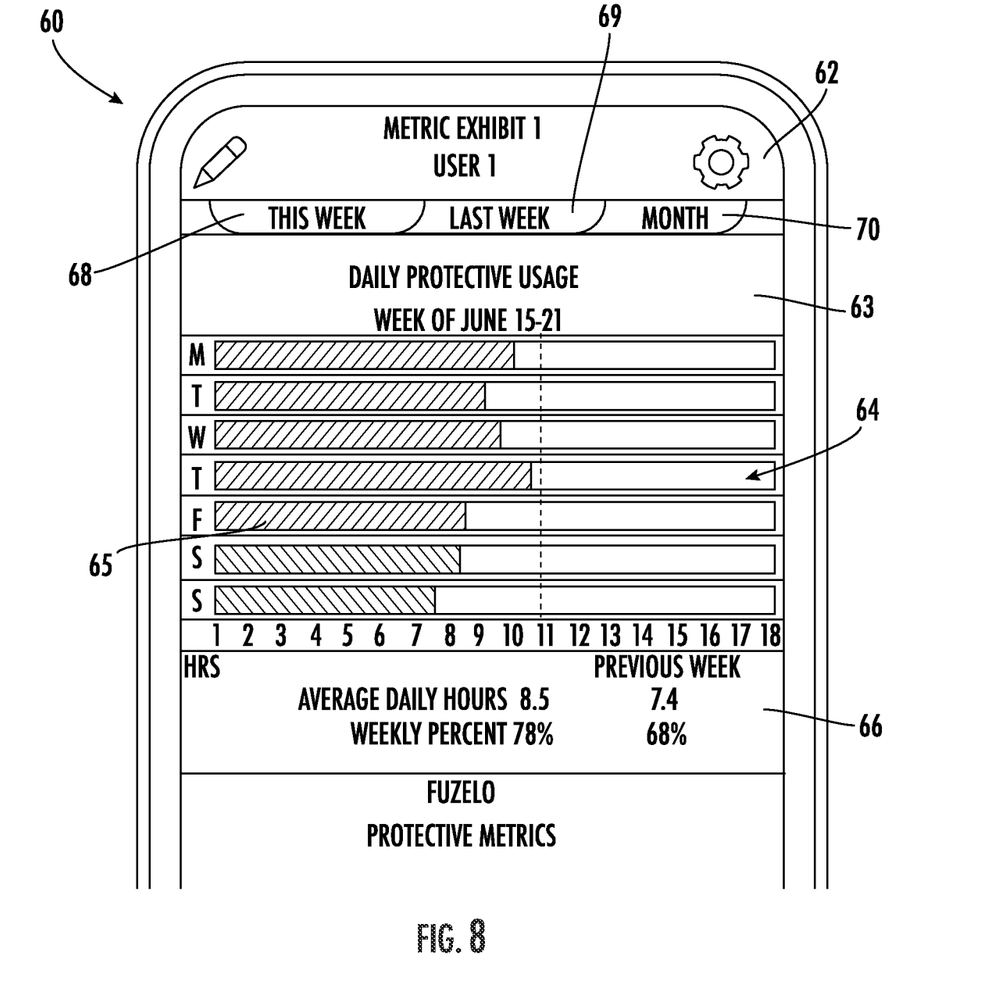
FIGS. 8-11 show display screens for a display unit associated a face shield tracking system.
Figure 9:
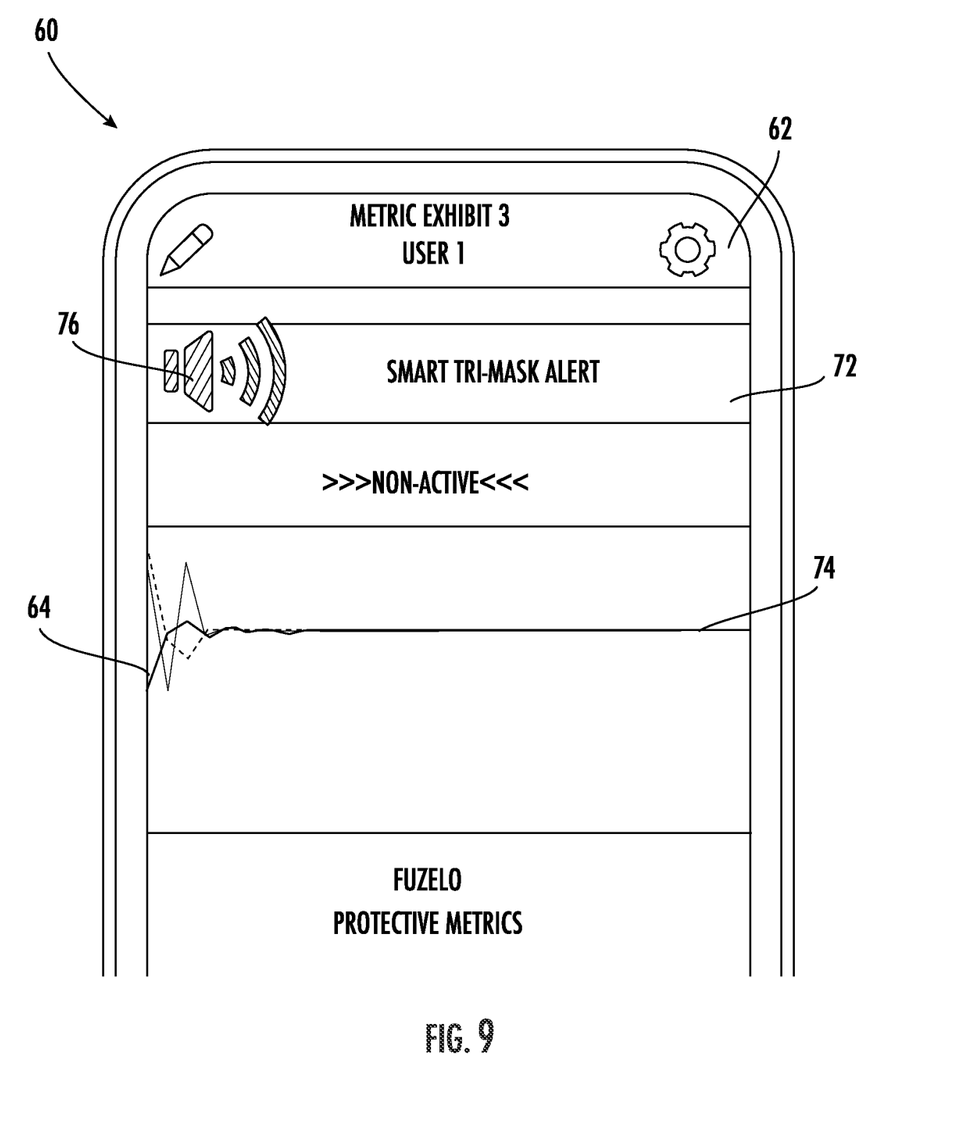
Figure 10:
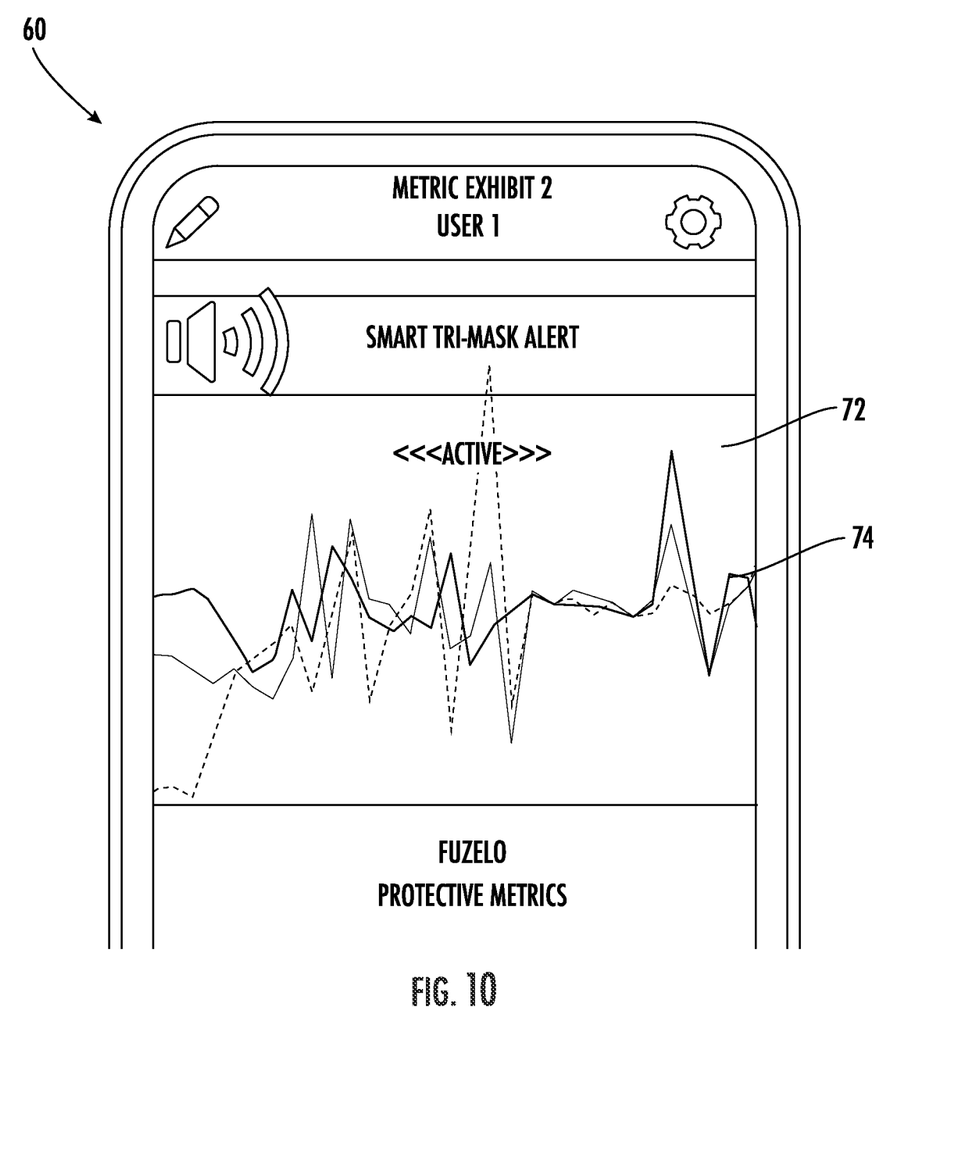

FIGS. 8-10 illustrate sample displays from a graphical user interface on the display device 60. The display of FIG. 8 includes an upper text area 62, a heading area 63, a graphical area 64, and a lower text area 66. The upper text area 62 includes identifying information such as the name of an individual such as an employee or student who has been assigned a face shield. The heading area 63 includes the title of the image shown in the graphical area 64, which in this case is a bar graph 65 showing the number of hours per day the wearer has worn the shield over the course of week. The display may also include several tabs 68, 69, 70 allowing the viewer to switch to different graphs, such as a graph showing the previous week's usage or a graph showing usage for the month. The lower text area 66 shows the wearer's average daily shield-wearing hours for the week compared to the hours for the previous week. The hours are also converted into percentages, showing how many hours the mask was worn in relation to the wearer's total number of hours at the institution being monitored.

The display of FIG. 9 retains the upper text area 62 of FIG. 8, but replaces the heading area of FIG. 8 with a status area 72. The graphical area 64 now displays a line graph 74 of the mask's activity over time. In this example, the line graph 74 has flattened, showing that the mask is not moving, which indicates that the individual to whom it has been assigned is probably no longer wearing it. This causes a "non-active" message to be displayed in the status area 72, and may also trigger an audible alarm, which may be accompanied by illumination of a speaker icon 76 in the status area.

The display of FIG. 10 is similar to that of FIG. 9 except that the line graph 74 now indicates that the mask is moving. This causes an "active" message to be displayed in the status area 72, and the speaker icon 76 to be dimmed.

Figure 11:
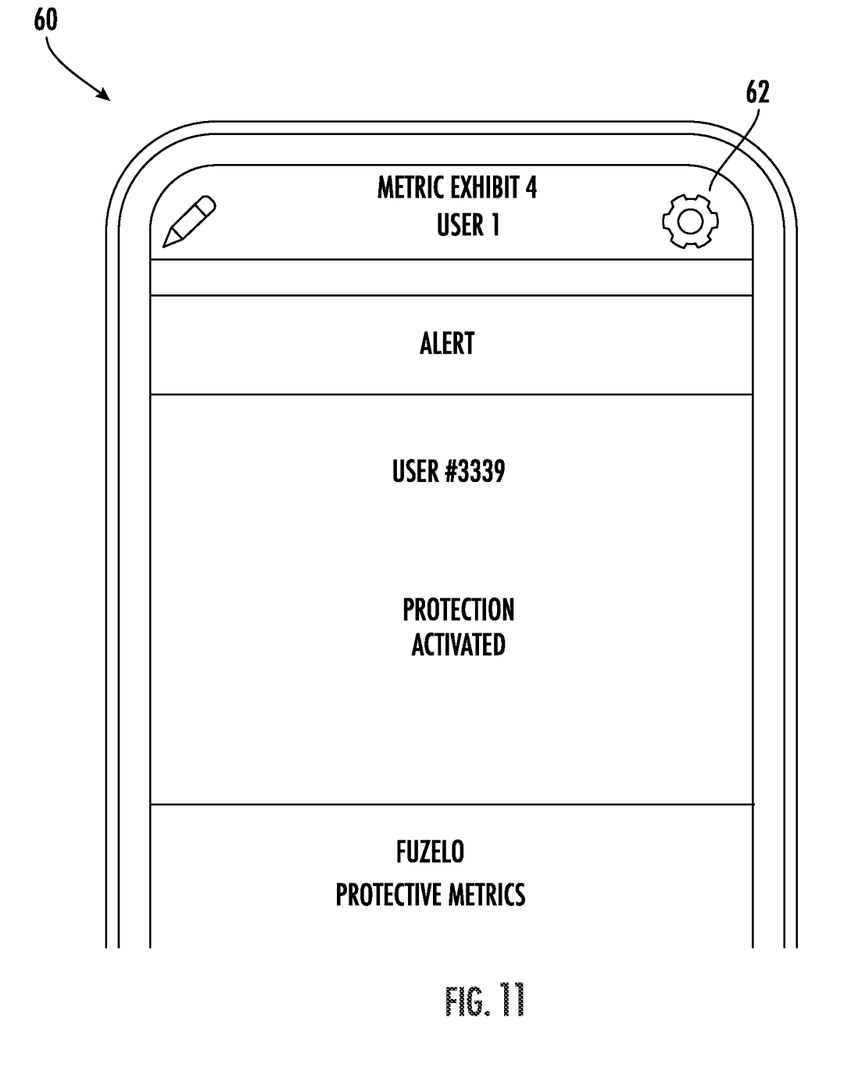

The display of FIG. 11 shows the user number of the individual identified in the upper text area 62 and indicates that the individual's face shield has been activated.

Other types of information that may be collected by the processor of the face shield tracking may include geographic and historic data that can be analyzed to identify incipient or potential outbreak areas and to initiate preventative protocols before high levels of transmission occur. In some embodiments, data and analytics collected and generated by the processor may displayed on augmented reality (AR) glasses built into or worn with the face shield.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A face shield comprising:
    a molded body portion configured to cover a wearer's eyes, nose, mouth, and chin, the body portion including:
        substantially planar eye regions configured to align with the wearer's eyes;
        a sloped nose region projecting outwardly relative to the eye regions and configured to align with the wearer's nose;
        cheek regions on either side of the nose region, each cheek region including a filtered opening; and
        a fairing formed rearwardly of each cheek region, each fairing containing a virus containment chamber having a front end communicating with the filtered opening in a respective one of the cheek regions and a rear end communicating with a respective filtered port in a rear portion of the respective fairing;
        a chin region configured to surround the wearer's chin; and
        a pair of temples extending rearwardly from the face shield and configured to secure the face shield to ears of the wearer.

2. The face shield according to claim 1, further comprising a seal surrounding both filtered openings and configured to sealingly engage the wearer's nose, cheeks, and chin.

3. The face shield according to claim 1, wherein:
    the body portion includes a back edge; and
    the back edge includes a series of baffles configured to direct air flow through circuitous paths and stop movement of aerosols carried in the air flow.

4. The face shield according to claim 2, further comprising a hinged door formed in the body portion and configured to provide access to the wearer's mouth, allowing the wearer to eat and drink without removing the face shield.

5. The face shield according to claim 2, wherein the temples are adjustably secured to the body portion.

6. The face shield according to claim 1, wherein the body portion is formed of a transparent plastic material.

7. The face shield according to claim 1, further comprising an inertial motion capture unit embedded into the face shield, wherein the inertial motion capture unit is configured to measure and record data about movements of the wearer.

8. The face shield according to claim 1, further comprising a temperature sensor embedded into the face shield, wherein the temperature sensor is configured to measure a body temperature of the wearer.

9. The face shield according to claim 1, wherein each fairing includes a side wall defining an entry scoop configured to direct incoming and outgoing air into the respective virus containment chamber.

* * * * *